United States Patent [19]

Scott, Jr.

[11] 4,275,716
[45] Jun. 30, 1981

[54] KNEE BRACE

[76] Inventor: Linzy Scott, Jr., 2085 Campbellton Rd., Atlanta, Ga. 30311

[21] Appl. No.: 78,186

[22] Filed: Sep. 24, 1979

[51] Int. Cl.³ .............................................. A61F 3/00
[52] U.S. Cl. .................................................... 128/80 C
[58] Field of Search .................... 128/80 C, 165, 87 R, 128/89 R; 2/22, 24

[56] References Cited

U.S. PATENT DOCUMENTS

| | | | |
|---|---|---|---|
| 3,581,741 | 6/1971 | Rosman et al. | 128/80 C |
| 3,669,105 | 6/1972 | Castiglia | 128/80 C |
| 3,804,084 | 4/1974 | Lehman | 128/80 C |
| 3,926,186 | 12/1975 | Nirschl | 128/165 |
| 3,945,046 | 3/1976 | Stromgren | 2/22 |

*Primary Examiner*—John D. Yasko

*Attorney, Agent, or Firm*—Newton, Hopkins & Ormsby

[57] ABSTRACT

A spiral-shaped knee brace which includes spaced, laterally extending rigid members which overlie and support the lateral and medial portions of the knee joint, a section which interconnects the rigid members and spans the popliteal region of the knee, a band that traverses the front of the upper thigh and is joined to one of the rigid members, a band that crosses the front of the lower tibia and is secured to the other rigid member and means for releasably securing the brace in its operative orientation about the knee. Valgus and varus stress and lateral and medial bending are blocked but the brace allows a selective amount of flexion of the knee and the rotation or locking home movement of the knee is not disrupted. Flexible and rigid embodiments of the brace are disclosed.

26 Claims, 6 Drawing Figures

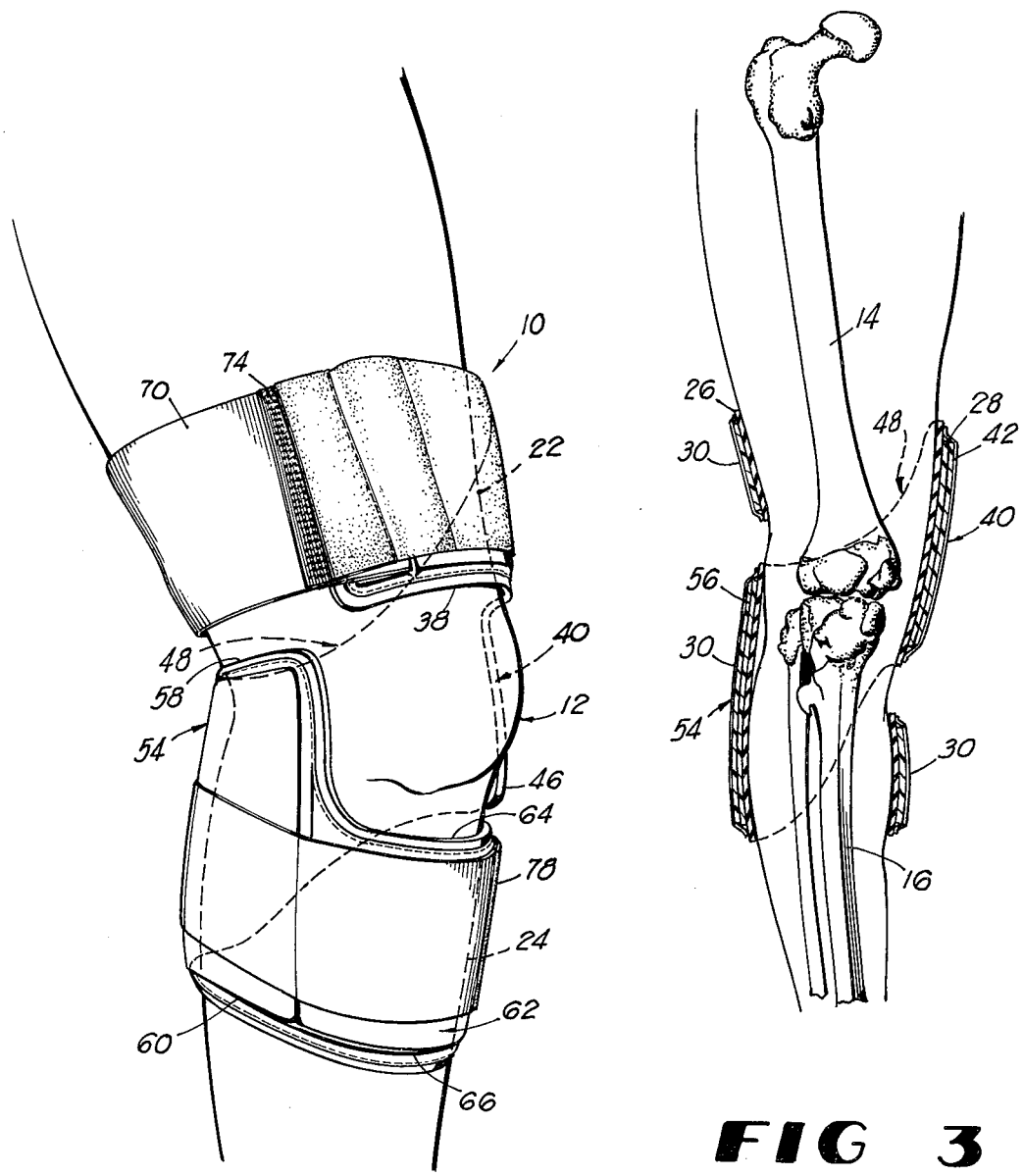
FIG 1
FIG 3
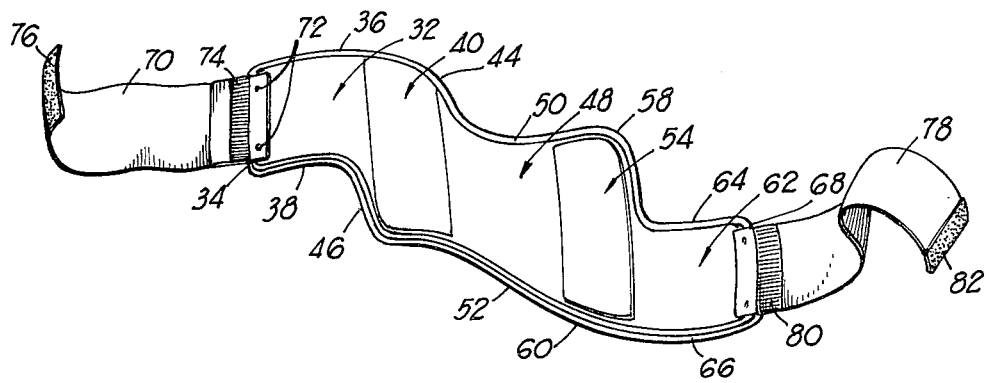
FIG 2

KNEE BRACE

BACKGROUND OF THE INVENTION

1. Field of the Invention

The present invention relates generally to an orthopedic appliance and, more particularly, to a knee brace.

2. Description of the Prior Art

The knee is the largest joint of the body formed generally by the hinge-joint of the thigh-bone (femur) above, the shinbone (tibia) below and the kneecap (patella) in front. That joint, which is capable of more movement than either those of the fingers or the elbows, is subject to many injuries due to its complex structure and the fact that it also has to sustain the greatest stresses since it supports the entire weight of the body and of the upper portion of the leg. Such injuries include a twisting or overextension of the knee joint. All knee injuries require a slow and gradual return to normal activity to avoid a recurrence and permanent crippling. In some instances, the knee must be immobilized to permit healing; in other cases, adequate support must be provided to the knee during the normal activity of the user.

The movements which take place at the knee joint are flexion and extension, and, in certain positions of the joint, medial and lateral rotation. The movements of flexion and extension at this joint differ from those in a typical hinge joint, such as the elbow, in that the axis around which motion takes place is not a fixed one, but shifts anteriorly during extention and posteriorly during flexion; and the commencement of flexion and the end of extension are accompanied by rotatory movements associated with the fixation of the limb in a position of great stability.

The typical prior art knee brace which permits flexion and extension of the knee includes a structure or framework which encircles the knee and which has a hinged joint. Since that brace forces the knee to move about that hinged joint, the knee is not allowed its normal movement of flexion because the axis around which the movement of the brace takes place is fixed. Additionally, the prior art braces do not allow rotation or the locking home mechanism of the knee joint.

Further, it is common for conventional knee appliances to be bulky and uncomfortable to wear. A number of the prior art devices have to be form-fitted to the user's knee. They also do not operate effectively in applying sufficient force on the user's knee due to their lack of three-point fixation.

SUMMARY OF THE INVENTION

The above disadvantages are overcome by the present invention which is a knee brace that, in its operative position embracing the user's knee, is generally in the form of a spiral and which prevents medial and lateral instability. The brace is of unitary construction and, in the first embodiment, is of flexible design so that it may be wrapped about the user's knee in the correct orientation and then may be removed therefrom to lie in a substantially flat plane.

In its planar, inoperable position, the brace of the first embodiment has opposed ends. Observing the brace for a right knee in that position and describing it from a front view, the device includes a band adjacent the left end which traverses the front of the upper thigh area immediately above the knee and terminates in a downwardly or laterally extending rigid pad which spans the medial portion of the knee. Attached to the medial pad is a section which crosses the popliteal space and terminates in a laterally projecting rigid pad which spans the lateral portion of the knee. The brace continues with a band that traverses the front of the lower tibia area and terminates in the right end of the device.

Means are provided for releasably securing the device in its spiral or cylindrical operative position about the knee and may include straps secured to the ends of the brace that have VELCRO fasteners on them with mating VELCRO fasteners on the respective thigh and tibia bands. The width of the section of the brace which is behind the kneecap is selectively adjustable along the length of the strap in order to provide the desired amount of flexion of the knee.

The first embodiment of the orthosis of the present invention comprises three layers which are stitched together, the innermost one that is adjacent the user's skin being PLASTAZOTE, the middle or stiffening layer being ORTHOPLAST and the outer layer being a covering of suitable material, such as cowhide. The medial and lateral pads are constructed of an extra thickness of ORTHOPLAST in order to provide the desired rigidity.

A second embodiment of the present invention is a rigid, spiral-shaped brace that is normally form-fitted for the user's knee and which cannot assume a planar position when it is not embracing the user's knee. The second embodiment may be constructed from polypropylene. As with the first embodiment, the second embodiment prevents medial and lateral instability of the knee by means of rigid pads which span the medial and lateral portions of the knee and which are joined together by a section which traverses the area behind the knee, the width of that section determining the amount of flexion of the knee permitted. The brace includes rigid bands which traverse the anterior upper thigh area and the lower anterior lower tibia area and which are affixed to the medial and lateral pads, respectively. Suitable securing means are provided on the bands to hold the brace in its correct orientation on the user's knee.

The above embodiments have been described in relation to a brace for a right knee. The brace for the left knee would be the mirror image of the brace for the right knee.

It is, therefore, the primary object of the present invention to provide an improved knee brace.

Another object of the present invention is to provide a knee brace which allows for flexion, extension and rotational movements of the knee.

A further object of the present invention is to provide a knee brace which prevents medial and lateral instability.

A still further object of the present invention is to provide a knee brace that has three-point fixation for stability, has no hinged joints and is lightweight and comfortable to use.

BRIEF DESCRIPTION OF THE DRAWINGS

FIG. 1 is a perspective view of the first embodiment of the present invention in its operational position embracing the user's knee;

FIG. 2 is a perspective view of the front of the first embodiment in its inoperative, planar position;

FIG. 3 is a front elevational, cross-sectional front view of the embodiment shown in FIG. 1;

DESCRIPTION OF THE PREFERRED EMBODIMENTS

Figure 4:
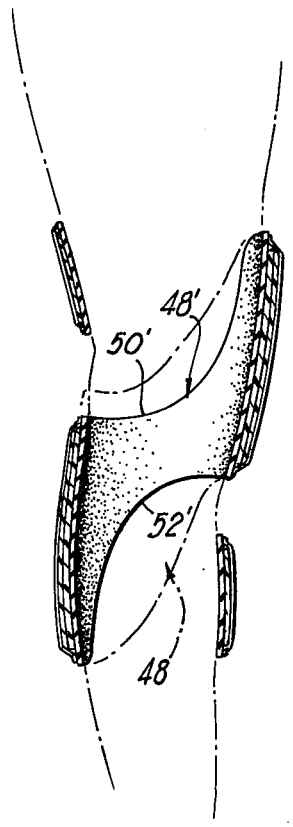
FIG. 4 is a front elevational, cross-sectional view of the brace of the first embodiment with a narrow second section.

Referring to FIG. 1 of the drawings, the numeral 10 denotes generally the first embodiment of the knee brace of the present invention in its operative position embracing the right knee 12 of the user. As seen in FIG. 3, the right knee 12 of a human includes the femur bone 14, the tibia bone 16, the medial portion 18 of the knee 12 and the lateral portion 20 of the knee 12. The anterior portion of the upper leg or thigh area above the knee 12 is denoted generally by the numeral 22, with the anterior of the tibia portion of the leg between the knee 12 being denoted by the numeral 24.

The brace 10 is of malleable construction so that it is capable of being moved from an inoperative, substantially planar position (as shown in FIG. 2) to an operative position wherein it embraces above and below the knee and the knee itself in a spiral configuration. The brace 10 includes an inner layer or sleeve 26 which overlies the skin of the user and which may be of a porous malleable material such as PLASTAZOTE, an inner layer 28 constructed of material which is more rigid than the inner layer 26 such as ORTHOPLAST and an outer layer 30 which may be of any suitable, durable material, such as cowhide. The layers 26, 28, 30 are joined together by any suitable means, such as stitching about the peripheral edges of the inner and outer layers 26, 30.

FIG. 2 shows the brace 10 for the right knee 12. The brace 10 is of unitary construction and is comprised of a plurality of integrally joined articulated parts. The brace 10 includes a first section or band which spans the anterior portion 22 and is comprised of an upright outer end 34 and parallel top and bottom edges 36, 38.

A first rigid means or pad 40 is adjacent first section 32 and has a second portion 42 of ORTHOPLAST material interposed between outer layer 30 and inner layer 28, as seen in FIG. 3. Upper edge 44 is joined to top edge 36 and gradually extends downwardly. Lower edge 46 of pad 40 downwardly extends from bottom edge 38 and is essentially L-shaped in design, thus having pad 40 laterally project below first band 32. The first pad 40 is dimensioned to span the medial portion 20 of the knee 12, as shown in FIGS. 1 and 3, including at least the medial femoral condylar portion of the knee 12.

The second section 48 of the brace 10 is dimensioned to traverse the posterior or popliteal region of the knee 12 and has top and bottom edges 50, 52 which are joined to upper and lower edges 44, 46, respectively. Second section 48 interconnects the second rigid pad 54 with the first pad 40.

The second pad 54 also includes an additional layer 56 of rigid material between the outer and inner layers 30, 28 and is dimensioned to span the lateral portion 18 of the knee 12, as shown in FIGS. 1 and 3, including at least the lateral tibia condylar portion of the knee 12. Upper edge 58 is integrally joined to top edge 50 and lower edge 60 is joined to bottom edge 52.

The third section 62 provides a means for traversing the anterior of the tibia or lower leg portion 24 below the knee 12 and has top and bottom edges 64, 66 which are joined together by outer edge 68 that is in opposed relationship to outer edge 34. The third section 62 is at a lower elevation than the first section 32, as seen in FIG. 2.

Means is provided for releasably securing the brace 10 in its operative, spiral configuration embracing knee 12 and includes a rectangular shaped, elongated, first flexible rubber strap 70 that is joined to the brace 10 adjacent outer edge 34 by any suitable means, including metal studs 72. As seen more clearly in FIG. 1, a portion 74 of VELCRO material is positioned on strap 70 adjacent studs 72 for interlocking engagement with a mating VELCRO portion 76 disposed on the opposite end of strap 70. The strap 70 is of sufficient length to extend at least about the posterior of the upper portion of the user's leg, as shown in FIG. 1. It is understood that VELCRO portion 74 could also be situated on section 32.

A second strap 78, which is similarly shaped as first strap 70, is joined to brace 10 adjacent outer edge 68 and includes VELCRO portions 80, 82 thereon. Strap 78 extends about the lower portion of user's leg below the knee 12, as seen in FIG. 1. VELCRO portion 80 could also be disposed on section 62.

The width of the second section 48 determines how much flexion of the knee 12 is permitted. FIG. 4 shows the brace 10 with a second section 48', with top and bottom edges 50', 52', that is narrower along its length than second section 48, thereby providing more flexion than with second section 48.

In case of a markedly unstable knee 12, it is possible to stabilize the same without the danger of knee collapse and without the patient falling by means of a wide posterior or second section 48, because it will "grab" beyond the allowable 20°-40° flexion. At the same time, a wide section 48 will allow the user to walk naturally and sit comfortably with the knee slightly flexed. The narrower posterior section 48' allows greater function without a noticeable change in support for those knees in which support of functional soft and semi-soft structures (ligaments, tendons and cartilages) is desired rather than support of the entire knee joint.

In the operation of brace 10, it is essentially wound about the upper and lower user's knee 12. The first section 32 is positioned on the anterior portion 22 so that the bottom edge 38 is just above the kneecaps. The first strap 70 is then snugly wrapped about the anterior portion 22 so that the portion 76 passes over the exterior of first section 32 and securely mates with portion 74.

The pad 40, section 48 and pad 54 will then automatically assume their respective correct, anatomical orientation about the knee 12 so that pad 40 will extend downwardly from section 32 and span the medial portion of knee 12, section 48 will traverse the rear of knee 12 and pad 54 will span the lateral portion of knee 12. Section 62 will then be positioned by the user to traverse the anterior portion 26 with upper edge 64 being just below the kneecap. The second strap 78 is secured about the lower leg so that VELCRO portion 82 is in engagement with portion 80.

With brace 10 in its operative position, valgus and varus stress and lateral and medial bending are blocked. A selective amount of flexion of the knee 12 is allowed, depending on the width of section 48. The rotation or locking home movement of the knee 12 is not prevented since the knee is allowed to extend fully about its own axes. As seen, the kneecap is exposed with brace 10.

Figure 5:
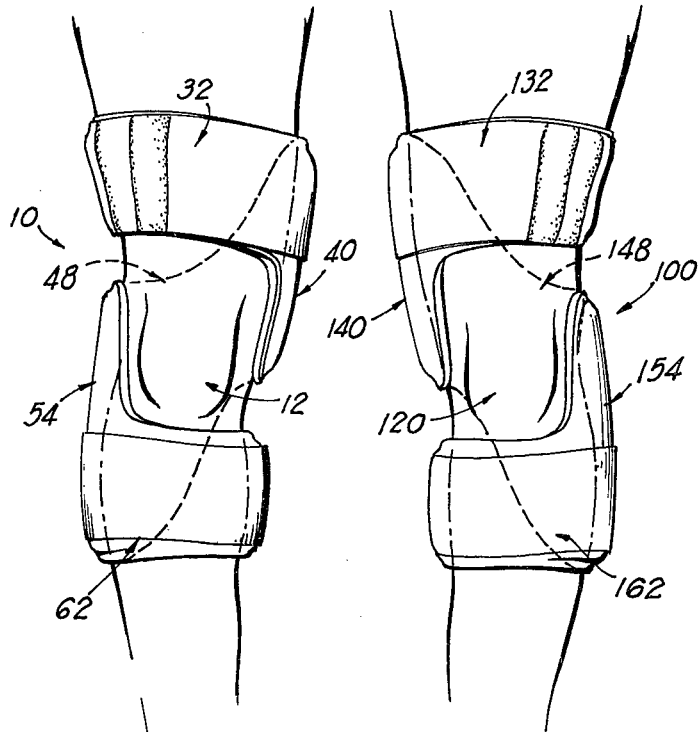
FIG. 5 is a front elevational view of the first embodiment of the brace in its operational position on the left and right knees.

The brace 10 has been described in relation to the right knee 12 but it can be seen in FIG. 5 that a brace 100 for the left knee 120 is the mirror image of brace 10, having first section 132, first rigid pad 140, second section 148, second rigid pad 154 and third section 162. Pads 140, 154 span the medial and lateral portions, respectively. As can be seen, regardless of whether it is brace 10 or brace 100, the respective pads on each brace are in spaced, opposed, staggered relationship along the longitudinal axes of the braces 10, 100 when they are in their respective operational positions about the knees.

Figure 6:
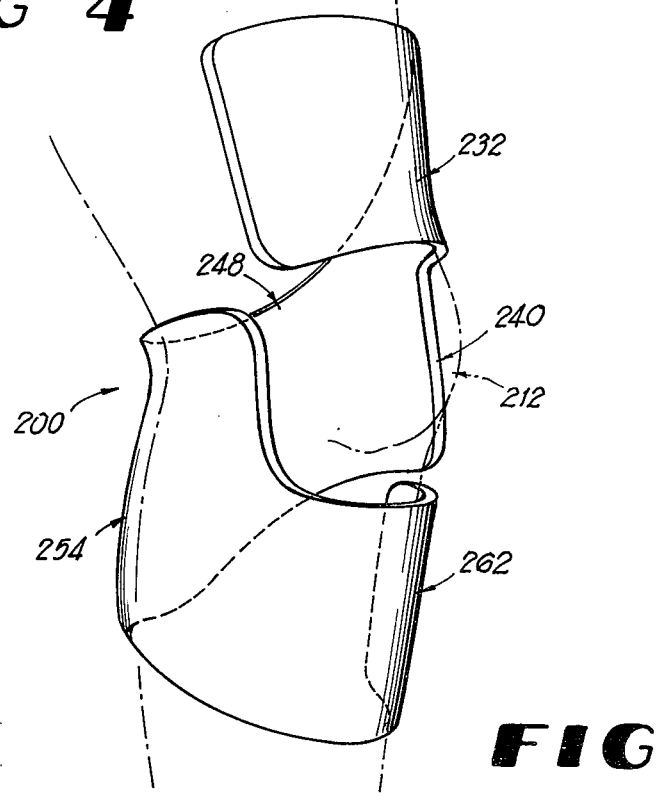
FIG. 6 is a perspective view of the second embodiment of the present invention.

The second embodiment 200 of the present invention is shown in FIG. 6 and is a brace of rigid construction which is not capable of assuming a planar position. Normally, the brace 200 would be fashioned from an actual case of the user's knee and related leg portions so as to provide a contour-fit. As with brace 10, the brace 200 is of unitary construction, preferably made of polypropylene, having a first section 232, a first or medial pad 240, a second section 248, a second or lateral pad 254 and a third section 262. All of the elements of brace 200 assume the same orientation about knee 212 as do the respective elements of brace 10.

The brace 200 may also be provided with releasable securing means, similar to straps 70, 78 but those are not shown in FIG. 6. The brace 200 is easily donned and removed from the user's leg by spiraling from the tibia upwardly or from the femor downwardly. The inner surface of brace 200 may be provided with a layer of polyurthane of sufficient thickness to provide a cushion so that the brace 200 does not irritate the skin. Also, a stockinette may be worn by the user and the brace 200 placed into position over that material.

Another adjustment means for the brace 200 may be an infrapatellar elastic band which may be detachably connected to the brace 200 so as to pull the medial pad 240 to the lateral pad 254. That provides stability medially and laterally, without significant loss of function or disruption of physiologic rotation.

Both brace 10 and brace 200 provide orthotic appliances which are not bulky and which present little resistance or hindrance to the normal movements of the knee joint, flexion, extension and the rotary "locking home" movement while simultaneously not allowing abnormal function of the knee, including medial, lateral, hyperextension, translation and excessive rotation. Constriction of movement is avoided, allowing a relatively free axis of rotation within physiologic limits (utilizing a "no force" principle). Since the present invention does not disrupt the individually variable "locking home" requirements of the knee, there is no resultant cumulative medial stress dangers to the medial meniscus and its allied structures. All of that is accomplished by the unique design of the present invention which utilizes the coil principle and its inherent resistance to deformation.

The present invention duly respects the time-honored three point fixation principle for an orthosis by virtue of the spiral design of both embodiments 10 and 200 giving greater stability and comfort with little sacrifice to function. The first three point fixation is comprised of the pads spanning the medial and lateral portions of the knee in conjunction with the posterior band. That fixation is reinforced by a second three point fixation comprising the two sections traversing the anterior portions of the leg above and below the knee (with the respective securing straps) when considered with the posterior band or the posterior band and the medial and lateral components taken together as a unit. Because of the coil principle, all of the above is accomplished without total rigidity although brace 200 may be constructed of rigid polypropylene.

Because of the three-point fixation of the present invention, the brace eliminates slippage. Further, there is little danger of "binding", constriction and/or pressure phenomenon occurring with the brace. Damage to the peroneal nerve is virtually eliminated because of the tibial spanning section. The brace of either embodiment is cosmetically appealing, light weight (approximately one pound for brace 200), water resistant and does not fatigue the user.

Users with severe low back syndromes may find the present invention very helpful for a neuro-muscular weak leg and knee but yet not stressful on the back. Low back irritation while wearing the brace may be lessened.

The present invention may be very helpful for the "giving away" knee, the ligamentous damaged knee, the patellar femoral syndrome, the "idiopathic painful" knee, post surgical synovitis, recurrent effusions and the elderly arthritic knee. Also, because of its coil or spiral design and its inherent resistance to deformation, the brace of the present invention yields yet another advantage as a possible extension aid. Therefore, it may have applicability in quadriceps insufficiency, in Osgood-Schlatters disease, patellar tendonitis, joggers' and tennis knees, and post-operative arthrotomy support.

The invention has been described in relation to a knee brace. However, it is understood that the brace is adaptable for use in connection with a brace for the elbow with the rigid pads scanning both sides of that joint, the middle or second section crossing the "crook" of the arm and the first and third sections traversing the upper and lower portions of the arm adjacent the elbow.

What I claim is:

1. An orthopedic appliance for the joint on a limb comprising: a first band which is adapted to traverse the anterior portion of said limb above said joint and which has opposed ends, a first rigid means that is joined at one of said ends of said first band and which extends downwardly so as to span a first side of said joint when said first band is on said anterior portion of said limb, a second band which is adapted to traverse the anterior portion of said limb below said joint and which has opposed ends, a second rigid means which is joined to one of said ends of said second band and which projects upwardly so as to span a second side of said joint when said second band is on said anterior portion of said limb, said first and second sides of said joint being in opposed relationship and a section being of sufficient length to cross the posterior portion of said joint and to interconnect said first and said second rigid means, said appliance capable of embracing said limb in a spiral-shaped configuration and having a longitudinal axis, said first and second rigid means being oriented on said appliance such that they are in spaced, staggered relationship along said axis.

2. An orthopedic appliance as claimed in claim 1 further including means for releasably securing said appliance in an operative position embracing said joint.

3. An orthopedic appliance as claimed in claim 1 wherein said section and first and second bands are constructed of malleable material.

4. An orthopedic appliance as claimed in claim 1 wherein said appliance is formed of a rigid material.

5. An orthopedic appliance as claimed in claim 4 wherein said material is polypropylene.

6. An orthopedic appliance for the joint on a limb which is capable of being moved from an inoperative planar position to an operative spiral configuration embracing said joint, said appliance being of unitary construction and having opposed ends and including a first section adjacent one of said ends and being of sufficient dimension to traverse the anterior portion of said limb above said joint when said appliance is in said operative spiral configuration; a first rigid pad laterally extending from said first section to overlie one side of said joint, a second section on said sleeve which is attached along one of the ends of said section to said first rigid pad and being of sufficient dimension to cross the popliteal region of said joint; a second rigid pad attached to the other end of said section and dimensioned to overlie the opposite side of said joint when said appliance is in said operative, spiral configuration; a third section adjacent the other of said opposed ends of said support and being attached to said second rigid pad, said third section being dimensioned to traverse the anterior portion of said limb below said joint when said appliance is in said operative spiral configuration; and means on said support for releasably securing said appliance in said operative spiral configuration.

7. A knee brace which in its operative position embraces a portion of the leg including the knee in a spiral-shaped configuration, said brace comprising first and second rigid means which are oriented in spaced relationship along the longitudinal axis of said brace when said brace is in said operative position so as to overlie each of the opposed sides of said knee; a band interconnecting said first and second rigid means and dimensioned to cross the rearward portion of the knee when said brace is in said operative position; a first section on which is dimensioned to traverse the femur portion of the leg when said brace is in said operative position and being connected to said first rigid means; and a second section which is dimensioned to traverse the tibia portion of the leg when said brace is in said operative position and being connected to said second rigid means.

8. A knee brace as claimed in claim 7 wherein said brace is constructed of malleable material.

9. A knee brace as claimed in claim 7 wherein said rigid means are in staggered relationship to each other along said brace.

10. A knee brace as claimed in claim 7 further including means for releasably securing said brace in said operative position.

11. A knee brace as claimed in claim 7 wherein said brace is constructed of rigid material.

12. A knee brace as claimed in claim 11 wherein said material is polypropylene.

13. A knee brace, comprising:
(a) a first means for spanning a first side of said knee, said first side including the medial femoral condylar portion of said knee;
(b) a second means for spanning a second side of said knee, said second side including the lateral tibial condylar portion of said knee and;
(c) means for crossing the posterior portion of said knee, said crossing means being connected to said first and second spanning means;
(d) a first means for traversing the anterior portion of the leg above said knee and being connected to said first spanning means; and
(e) a second means for traversing the anterior portion of the leg below said knee and being connected to said second spanning means.

14. A knee brace as claimed in claim 13 wherein said brace is constructed of a rigid material.

15. A knee brace as claimed in claim 13 wherein said brace is constructed of polypropylene.

16. A knee brace as claimed in claim 14 including a layer of polyurethane on the interior surfaces of said brace and being of sufficient thickness to act as a padding.

17. A knee brace as claimed in claim 13 further including means for releasably securing said brace on said knee.

18. A knee brace as claimed in claim 13 further including first means on said first traversing means for releasably embracing said first traversing means to said anterior portion of said leg above said knee.

19. A knee brace as claimed in claim 13 further including second means on said second traversing means for releasably embracing said second traversing means to said anterior portion of said leg below said knee.

20. A knee brace as claimed in claim 18 wherein said first embracing means includes a flexible strap having opposed ends, one of said ends being attached to said first traversing means and said strap being of sufficient length to at least extend about the posterior portion of the leg above said knee so that the other of said ends of said strap is capable of being datachably connected to said first traversing means.

21. A knee brace as claimed in claim 10 wherein said second embracing means includes a flexible strap having opposed ends, one of said ends being attached to said second traversing means and said strap being of sufficient length to at least extend about the posterior portion of the leg below said knee so that the other of said ends of said strap is capable of being detachably connected to said second traversing means.

22. A knee brace as claimed in claim 13 wherein said brace is capable of being moved from an inoperative, substantially planar position to an operative position embracing the knee, said brace comprising a first layer which is adjacent the skin of the leg and which is a second layer of material adjacent said first layer and which is constructed of material which is more rigid than said malleable material and means for joining together said first and second layers.

23. A knee brace as claimed in claim 22 wherein said malleable material is PLASTAZOTE.

24. A knee brace as claimed in claim 22 wherein said material of said second layer is ORTHOPLAST.

25. A knee brace as claimed in claim 22 wherein said first and second spanning means are of more rigid construction than said crossing means and said first and second traversing means.

26. A knee brace as claimed in claim 22 further including means for releasably securing said brace in said operative position.

* * * * *